(12) United States Patent
Buckland et al.

(10) Patent No.: US 9,375,511 B2
(45) Date of Patent: Jun. 28, 2016

(54) BONE-REPLACEMENT MATERIALS, METHODS AND DEVICES

(75) Inventors: Thomas Buckland, Aylesbury (GB); Charles Campion, Barnet (GB); James J. Cassidy, Foley, MN (US)

(73) Assignee: ApaTech Limited, Elstree, Hertfordshire (GB)

( * ) Notice: Subject to any disclaimer, the term of this patent is extended or adjusted under 35 U.S.C. 154(b) by 1009 days.

(21) Appl. No.: 12/528,923

(22) PCT Filed: Feb. 27, 2008

(86) PCT No.: PCT/GB2008/000648
§ 371 (c)(1),
(2), (4) Date: Aug. 18, 2010

(87) PCT Pub. No.: WO2008/104762
PCT Pub. Date: Sep. 4, 2008

(65) Prior Publication Data
US 2010/0324500 A1    Dec. 23, 2010

(30) Foreign Application Priority Data

Feb. 27, 2007   (GB) .................................. 0703763.3

(51) Int. Cl.
*A61L 27/12* (2006.01)
*A61L 27/28* (2006.01)
*A61L 27/54* (2006.01)

(52) U.S. Cl.
CPC .................. *A61L 27/12* (2013.01); *A61L 27/28* (2013.01); *A61L 27/54* (2013.01); *A61L 2300/418* (2013.01); *A61L 2300/606* (2013.01); *A61L 2430/02* (2013.01)

(58) Field of Classification Search
CPC .................. A61L 2300/418; A61L 2300/606; A61L 2430/02; A61L 27/12; A61L 27/28; A61L 27/54
See application file for complete search history.

(56) References Cited

U.S. PATENT DOCUMENTS

| 6,053,970 | A | * | 4/2000 | Ison et al. ........................ 106/35 |
| 2002/0054914 | A1 | * | 5/2002 | Morcol et al. ................. 424/491 |
| 2002/0161449 | A1 | | 10/2002 | Muschler |
| 2003/0180371 | A1 | * | 9/2003 | Reslow et al. ................. 424/493 |
| 2003/0195629 | A1 | * | 10/2003 | Pafford et al. ............. 623/17.16 |
| 2007/0031515 | A1 | * | 2/2007 | Stucky et al. .................. 424/724 |
| 2009/0252805 | A1 | * | 10/2009 | Piene ............................ 424/490 |

FOREIGN PATENT DOCUMENTS

| JP | 2004024319 A | 1/2004 |
| JP | 2005152653 A | 6/2005 |
| JP | 2006271521 A | 10/2006 |
| WO | 01/28448 A2 | 4/2001 |
| WO | 02/067820 A1 | 9/2002 |
| WO | 2006/015275 A2 | 2/2006 |
| WO | 2006/058153 A1 | 6/2006 |
| WO | WO 2006058153 A1 * | 6/2006 |

OTHER PUBLICATIONS

K.A.Hing, et al, "Effect of Silicon Level on Rate, Quality and Progression of Bone Healing Within Silicate-substituted Porous Hydroxyapatite Scaffolds", Elsevier, Science Direct, Biomaterials 27 (2006) 5014-5036.
International Search Report, mailing date Mar. 5, 2009 in related application No. PCT/GB2008/000648.
Search Report of Jun. 7, 2007 in related GB0703763.3.

* cited by examiner

*Primary Examiner* — Kyle Purdy
(74) *Attorney, Agent, or Firm* — Bret E. Field; Makoto Tsunozaki; Bozicevic, Field & Francis LLP

(57) ABSTRACT

A bone graft material is provided comprising granules of synthetic bone material, at least some of which have a solid coating comprising a blood-clotting agent. A device for delivering bone-replacement material to a an area to be treated is also provided, the device comprising: a chamber for containing bone-replacement material, wherein the chamber is pre-loaded and/or pre-coated on an interior surface thereof with a blood-clotting agent; means for introducing bone-replacement material into the chamber to contact the blood-clotting agent; and a means for delivering the bone-substitute material from the chamber to the area to be treated.

19 Claims, 1 Drawing Sheet

BONE-REPLACEMENT MATERIALS, METHODS AND DEVICES

The present invention relates to bone-replacement materials, methods and devices.

Bone-replacement materials are used in the replacement, repair or augmentation of damaged bones and joints. As such, the global interest in bone-replacement materials is ever increasing as a result of the developed world's aging population and the population's accompanying increasing expectations about their quality of life. To meet this demand, there is a need for bone-replacement materials that are reliable in their properties and easy and convenient to administer to a patient.

Traditionally, transplanted bone has been used when a bone-replacement material is required. This transplanted bone may be either obtained from a donor (when it is called an allograft) or from another site in the patient being treated (when it is called an autograft). However, these transplant techniques face limitations of supply and consistency of the transplanted product. Therefore, synthetic bone-replacement materials have been developed.

Synthetic bone-replacement materials can be used as a replacement for transplanted bone. Alternatively, they may be used in conjunction with transplant techniques, effectively filling in the gaps between the transplanted bone and the bone already present at the treatment site. The exact role of the bone-replacement material will depend on its function. For example, bone-replacement materials may be suitable for use for the filling of both load bearing and non-load bearing osseous defects, such as in joint and facial reconstruction.

'Natural' bone can be described as a matrix made from an inorganic component and an organic component. The matrix acts as a scaffold for the living component of the bone, which comprises bone cells. As such, the matrix is described as osteoconductive, because bone cells attach themselves to it and grow on it. The inorganic component of the matrix is hydroxyapatite $(Ca_{10}(PO_4)_6(OH)_2)$, which serves as the rigid component of the matrix, giving strength to the bone structure. The organic component is mainly Type I collagen, which acts to increase bone's elasticity and fracture resistance.

Synthetic bone-replacement materials effectively try to mimic some of the properties of the matrix material in natural bone. In order to achieve this, synthetic bone-replacement materials typically comprise the following components:
 (i) an osteoconductive material;
 (ii) optionally a carrier; and
 (iii) optionally osteoinductive additives.

The osteoconductive material may be a ceramic material. Such materials include calcium phosphates, such as the apatite group of minerals, which are favoured because of their similarity to the inorganic component of natural bone. The apatites are a form of calcium phosphate, with stoichiometric hydroxyapatite having a molar ratio of Ca/P of 1.67. This similarity between these minerals and the inorganic component of bone is accompanied by the strong biocompatibility of the apatite materials. There are many forms of 'bone powder' that incorporate calcium phosphate currently on the market that have been used in bone-substitute materials. Alternatively, some formulations are mainly based on the organic component in natural bone (e.g. collagen).

The second component in a synthetic bone-replacement material is generally a carrier. This is used to deliver the osteoconductive material to the treatment site. The carrier then dissolves under physiological conditions over time, leaving behind an inorganic scaffold. The carrier may simply serve to transform the dry osteoconductive material into a slurry; it may also be provided as a gel. Alternatively, some bone-replacement materials may be supplied without a carrier, e.g. in dry granule form.

The third component, which is optionally added, is an osteoinductive additive. This class of additives serves to stimulate the growth of bone cells on the scaffold. Osteoinductive additives may include growth factor, such as PGF-$\beta$ growth factor. The osteoconductive material may also act as an osteoinductive additive.

Previously, there has always been a balance between, on the one hand, optimizing the composition of the bone-replacement material so that it is easy to handle and to administer to a patient and, on the other hand, optimizing the composition so that it effectively mimics the role of natural bone. Ideally, a bone-replacement material would be delivered to the treatment site without the use of a carrier. This is because a carrier, when dissolved over time in the body, can act to mobilize the osteoconductive component, weaken its structure and even move it away from the treatment site. In addition, the time taken for carrier to be removed from the treatment area can be significant. This causes a retardation of the bone growth cascade, and it may lead to a reduction in the performance of the bone-replacement material.

However, simply delivering dry granules of an osteoconductive material to the treatment site is also unsatisfactory. Dry granules are difficult to place at the treatment site and can carry electrical charge, which tends to cause them to scatter.

One different approach is the use of a patient's own blood as the carrier in a bone-replacement material. This is, for example, described in WO01/28448, which relates to a method for preserving the bone material around an extracted tooth root socket. In this document, it is described how blood, once extracted from the patient and mixed with the bone-replacement material, should be allowed to congeal for 2 to 4 minutes, at which time the mixture is administered to the treatment area.

The inventors of the present invention have recognised that this type of method may be advantageous for a number of reasons. Firstly, clotted blood is not dissolved in the body as other carrier formulations are; instead, it is broken down by cellular action. This means that there are fewer problems associated with the carrier facilitating the removal of the osteoconductive material from the active site. In addition, blood contains many proteins appropriate for bone cell attachment and wound repair. As such, the carrier can also act as an osteoinductive component. This is taken advantage of in, for example, WO2006/015275. Furthermore, it has been shown that blood contains viable mesenchymal stem cells, which are bone cell precursors. Therefore, it is possible that growth of living tissue on the scaffold of the bone-replacement material is further enhanced.

However, there are drawbacks associated with this simple method of extracting blood, mixing it with the bone-replacement material and allowing it to congeal for a short time. In particular, the properties of the resulting formulation are not predictable. The present inventors have now recognised the importance of the viscosity of the mixture administered to the patient. For example, if the viscosity is too low, the bone-replacement material will simply drain away from the treatment site. It is therefore necessary to be able to reproducibly produce a solution of desired viscosity. The cohesiveness, tackiness and mouldability of the formulation are important for similar reasons.

When using blood as a carrier, the viscosity (and cohesiveness, tackiness and mouldability) depends on the degree of congealing of the blood. The degree of congealing is, in turn, dictated by the rate of congealing. However, this is very dependent on the particular patient: some patients' blood congeals very quickly, while others' congeals slowly. Therefore, when using blood as a carrier of a bone-replacement material, it is difficult to reproduce a desired viscosity of the bone-replacement material.

In view of this drawback, most currently-used bone-replacement materials contain their own (usually synthetic) carrier to control the viscosity of the material. When the use of blood-derived products is contemplated, as in WO2006/058153, this is the accompanied by the use a specialized and complicated mixing and delivery device.

The present invention aims to addresses at least some of the problems associated with the prior art. In particular, the present inventors have found ways to reproducibly obtain a bone-replacement material of a desired viscosity and using congealed blood as the carrier of the bone-replacement material.

As used herein, synthetic bone material refers to calcium phosphate-based materials wherein the calcium phosphate material is not directly derived from a human or 'living' source. It is contemplated by the present invention that this can be mixed with or used in conjunction with bone graft material derived from human or 'living' source. In addition, although calcium phosphate materials are preferred synthetic bone materials, the definition of synthetic bone material also includes synthetic materials (i.e. materials not directly derived from a living source) that replicate the organic component of natural bone, for example collagen-based materials.

Calcium phosphate refers to materials that comprise calcium and phosphate. The stoichiometry of the two components within the materials is not limited. However, the stoichiometry of calcium to phosphate is preferably between 1:1.5 to 1:2, and more preferably around 1.67. The term includes within its scope products containing calcium phosphate together with other components, for example silicon. This is the case for silicon-substituted hydroxyapatite.

Granules is a general term that simply refers to a product that is not supplied as a single, integral, uniform product. As such, the size of the individual granules is not limited and nor is the size distribution of the granules. However, preferably at least 90% (more preferably 95%) of the granules will have a diameter in the range of between 0.1 and 10 mm, preferably between 0.5 and 5 mm. (The diameter is by a conventional methods, for example by measuring the maximum dimension of (e.g.) 100 particles by optical microscopy (if appropriate) and taking the mean of the results).

The granules may be porous or solid. However, when using calcium phosphate materials, it will usually be expected that the granules are porous. The particles may also be approximately spherical.

Blood clotting agents refers to all materials, both natural and synthetic, that play a role in the coagulation of blood. As such, the definition of blood clotting agents includes materials that initiate and/or are involved in primary haemostasis and secondary haemostasis. The definition of blood clotting agents also includes within it cofactors (such as calcium ions) that play a role in the coagulation of blood.

A bone graft material is a precursor material to a bone-replacement material. In the present invention, it is preferable that the bone graft material can simply be mixed with a blood product (for example, whole blood) to produce a bone-replacement material.

References to 'blood' refer to both blood and blood-derived products. References to 'whole blood' refer only to blood that has not been processed. In the present invention, preferably whole blood is extracted from a patient needing bone-replacement treatment and mixed with the bone graft material to form the bone replacement material. The patient's own blood can be extracted and mixed with the bone graft material either immediately or having been stored under normal conditions for a period of time.

Figure 1A:
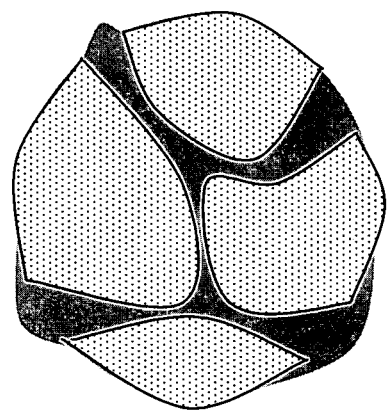
FIGS. 1A to 1C illustrate various coated granules in accordance with embodiments of the invention.

The present invention will now be described. In the following passages, different aspects of the invention are defined in detail. Each aspect so defined may be combined with any other aspect or aspects unless clearly indicated to the contrary. In particular, any feature indicated as being preferred or advantageous may be combined with any other feature or features indicated as being preferred or advantageous.

Accordingly, in a first aspect, the present invention provides a bone graft material comprising granules of synthetic bone material, at least some of which have a solid coating comprising a blood-clotting agent.

By coating the synthetic bone granules with a blood-clotting agent, either partially or completely, a bone-replacement material can be obtained with predictable viscosity properties when the bone graft material of the present invention is mixed with blood. In particular, there is no need to determine how much blood-clotting agent should be mixed with the synthetic bone granules at the point of use because the bone graft material is provided with the blood-clotting agent pre-loaded onto the synthetic bone material. This means that the use of the bone graft material is more convenient and more predictable compared to a synthetic bone graft material and a blood-clotting agent provided separately.

Furthermore, because the blood-clotting agent is coated onto the synthetic bone granules, blood coagulation is initiated at the surface of the synthetic bone material. The present inventors have found that this may be advantageous because the osteoinductive components of the clotted blood are provided directly at the surface of the synthetic bone material. In contrast, in bone graft materials where a blood-clotting agent and synthetic bone-material have been provided separately, coagulation of the blood is not initiated at the surface of the synthetic bone material and osteoinductive components contained in the clotted blood may not be so closely associated with the synthetic bone material. Therefore, actually coating the blood-clotting agent onto the synthetic bone granules may help to induce bone-growth at the surface of the synthetic bone material when administered to a treatment site in a patient. This may lead to a more 'natural' or 'stronger' bone replacement material.

Methods for coating the blood-clotting agent onto the synthetic bone granules include chemically bonding a clotting agent to the surface of the granules; absorbing the clotting agent into the pores of granules (if the granules are porous) or adhering a surface coating which contains the clotting agent to the surfaces of granules.

The relative amounts of the synthetic bone material and clotting agent are chosen according to the preferred properties of the final bone-replacement material. For example, if a dense bone-replacement material is required, there is a balance between maximizing the amount of synthetic bone material in the bone graft material and having sufficient clotting agent present so that the bone graft material can be wetted with a minimum of blood.

The inventors have found that there should preferably be a minimum amount of synthetic bone material in the bone graft material so that it is effective as a bone-replacement material.

Preferably, the mass of the synthetic bone material is 60% or more of the combined mass of the blood-clotting agent and the synthetic bone material. More preferably, it is 80% or more. More preferably, it is 90% or more.

The inventors have also found that there should preferably be a minimum amount of blood-clotting agent present. If there is too little, the blood-clotting agent will have a lesser effect on the rate of clotting of blood, and the clotting process will become more dependent on the properties of the blood itself rather than on the properties of the bone graft material containing the blood-clotting agent. Therefore, a minimum amount of blood-clotting agent is preferably present so that the blood-clotting properties of the bone graft material are more predictable. Preferably, the mass of the blood-clotting is 2% or more of the combined mass of the blood-clotting agent and the synthetic bone material. More preferably, it is 5% or more.

Figure 1B:
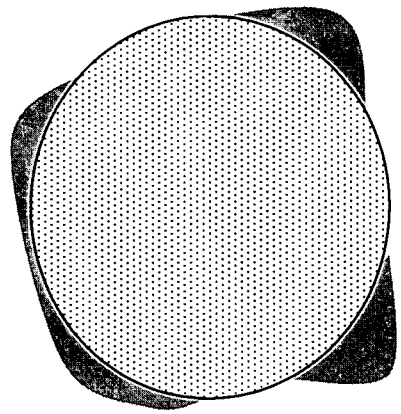
Figure 1C:
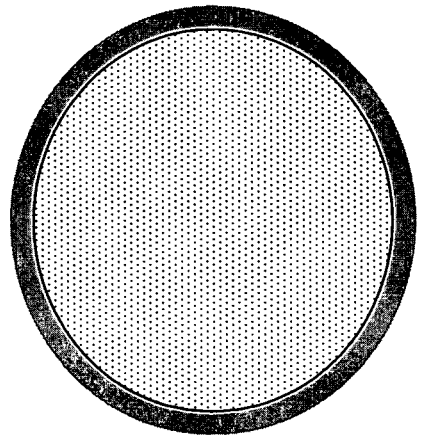

In this embodiment of present invention, the synthetic bone granules are coated with a blood-clotting agent. The coating on the bone granules may completely cover the granules, as illustrated in FIG. 1C, or it may be present only on parts of the surface of the granules, as illustrated in FIGS. 1A and 1B. For example, when using granules that are porous to the blood-clotting agent, the granules may absorb the blood-clotting agent, causing the coating layer to form over the pores of the granules, as illustrated in FIG. 1A. The blood-clotting agent may then go on to form over the solid surfaces of the granules.

However, in order to gain the beneficial effects of having the blood-clotting agent contained in a layer coating the synthetic bone material, preferably the solid coating covers 50% or more of the outer surface of the synthetic bone material. More preferably, the solid coating covers 90% or more of the outer surface of the synthetic bone material.

The extent of the absorption of the blood-clotting agent on the surface of the granules may be measured by optical reflectance light microscopy of embedded and polished coated granules.

The bone graft material of the present invention may be mixed with whole blood (autologous or allogenic) or any blood-derived product, such as platelet-rich plasma. The blood-derived product is any product that contains purified blood extracts. As such, it may be one or more of platelet-rich plasma, packed red blood cells, granulocyte concentrates, platelet concentrates, fresh frozen plasma, freeze-dried plasma, any other form of human plasma, plasma protein fraction, human albumin 25% and cryoprecipitate. However, the bone graft material is preferably for mixing with whole blood (i.e. unprocessed blood). Autologous blood is also preferred over donor blood. Autologous blood may have the advantage over donor (allogenic) blood because there is no worry about infecting a patient with undetected viruses, pathogens or the like. Furthermore, it is usually convenient to extract blood from a patient just before treatment with the bone-replacement material. In addition, there may be less risk when using autologous blood that the bone-replacement material will be rejected by the body. However, donor blood may also be used when considered appropriate.

Although it is preferable to use only whole blood under most situations, it is also possible to use processed blood products (i.e. blood-derived products) either by themselves or in combination with the 'whole' blood. This is because it is not always convenient to use whole blood. In addition, when treating frail patients, it may not be desirable to extract a lot of blood from the patient.

Therefore, a small amount autologous (or, as appropriate, allogenic) blood may sometimes be 'topped up' with a processed blood product. For example, the blood may be topped up with a component that allows for more predictable clotting behaviour or more beneficial bone-forming behaviour.

Preferably, the synthetic bone material comprises calcium phosphate. The synthetic bone material may be, for example, any of the apatite group of minerals including hydroxyapatite. This includes the use of substituted (e.g. Si-substituted) apatites/hydroxyapatites.

Preferably, the clotting agent comprises one or more of calcium chloride, zeolite, chitosan, ferrate (VI) salts, clotting factor VIII, clotting factor Xa, clotting factor XIIa and tissue factor. The clotting agent may be fibrinogen, trnasglutinamase or any of the regulatory proteins that play a role in blood clot formation or maintenance. Preferably, the clotting agent is one or both of calcium chloride and a zeolite. These are preferred clotting agents because they are non-pharmaceutical agents that do not need to be derived from either the patient, animal sources or via (inconvenient) recombinant methods.

Preferably, a dehydration agent is included in the bone graft material. The presence of a dehydration agent, which removes water from the liquid phase of the bone-substitute material, increases the rate of clotting during the clotting process. In some cases, for example when zeolite is used, the dehydration agent may also act as a clotting agent.

In a second aspect, the present invention also relates to a method for forming a bone-replacement material, as well as the bone-replacement material produced by this method. In particular, the present invention also relates to a method of forming a bone-replacement material, the method comprising mixing:

(a) whole blood; and
(b) a bone graft material comprising a synthetic bone material and a blood-clotting agent.

As noted in relation to the first aspect of the present invention, it is more convenient to provide a synthetic bone material and a blood-clotting agent together because this can lead to greater reproducibility in the formation of the bone-replacement material. There are additional benefits, as described in relation to the first aspect of the present invention, when the blood-clotting agent is provided as a coating on the synthetic bone material. Therefore, preferably the bone graft material used in the method described above is the bone graft material described in relation to the first aspect of the present invention.

Preferably, a dehydration agent is added to the bone graft material used in this second aspect. The preferred dehydration agents described in relation to the first aspect of the present invention apply equally to this second aspect.

In addition, the preferred blood-clotting agents and synthetic bone materials described in relation to the first aspect of the present invention apply equally to this second aspect.

Preferably, 1 part by volume of the bone graft material is added to 0.05 to 25 parts by weight of whole blood. If the bone graft material is added to less than 0.05 volume parts of blood, the bone-replacement material may not exhibit the preferred viscosity properties. If the bone graft material is added to more than 25 volume parts of blood, the bone-replacement material may be too fluid and not dense enough. More preferably, 1 part by volume of the bone graft material is added to 0.1 to 10 parts by volume of whole blood, more preferably 0.5 to 1.5, more preferably about 1. The volume of the bone graft material may be measured by pouring the bone-graft material into a container, allowing the material to settle in the container for several minutes (e.g. 30 minutes) and measuring the volume of the powder.

Preferably, the product of the method of this second aspect is cohesive, mouldable, capable of being cut into blocks without breaking up and capable of supporting its own weight when picked up. Preferably, the product is formed within 10 minutes of mixing the bone graft material and the blood, more preferably within 5 minutes, for example within 2 minutes. The product is then administered to the area-to-be treated.

The present inventors have found an alternate solution to the problem of providing an advantageous bone-replacement material in which blood acts as a carrier for a bone-graft material. In this third aspect of the present invention, a device is provided that may be used in the treatment of damaged bones or joints and also in the preparation of a bone-substitute material. The device comprises:
- a chamber for containing bone-replacement material, wherein the chamber is pre-loaded and/or pre-coated on an interior surface thereof with a blood-clotting agent;
- means for introducing bone-replacement material into the chamber to contact the blood-clotting agent; and
- a means for delivering the bone-substitute material from the chamber to the area to be treated.

Thus a device is provided that may allow the predictable, reproducible clotting of blood before administering it to an area-to-be treated.

Preferably, the device is a syringe comprising a chamber coated with a blood-clotting agent, which can be used to administer bone-substitute material to a patient.

The device according to the present invention is designed for use in an in situ method of clotting blood contained in a bone-replacement material. As such, it is ideal for use in conjunction with a bone-replacement material comprising autologous blood as the carrier (i.e. blood from the patient under treatment). As described in relation to the first aspect of the present invention, it is preferable to use whole blood (either autologous or allogenic) on its own. However, when considered appropriate, whole blood 'topped up' with processed blood products, or processed blood products may be used on their own.

The means for introducing bone-replacement material into the chamber will typically simply comprise an inlet, preferably a sealable inlet.

The means for delivering the bone-substitute material from the chamber to the area to be treated will typically simply comprise an outlet, preferably a sealable outlet. It is envisaged that the inlet may also serve as the outlet. Pump means may also be provided to facilitate delivery of the bone-substitute material from the chamber to the area to be treated.

Preferably, a dehydration agent may also be added, either before or during the clotting process. The dehydration agent may also be pre-loaded in the chamber or pre-coated on the inside of the chamber of the device of the present invention, alongside the clotting agent. The preferred dehydration agents described in relation to the first aspect of the present invention apply equally to this third aspect.

In addition, the preferred blood-clotting agents and synthetic bone materials described in relation to the first aspect of the present invention apply equally to this second aspect. Preferably, the clotting agent is calcium chloride because the present inventors have found that this may be conveniently coated on the inside of a device according to the present invention. For similar reasons, another convenient substance is a zeolite.

The chamber in the device of the present invention may be either partially or fully coated with the blood clotting agent and optionally the dehydration agent. This enables control of the amount of blood clotting agent that is exposed to the bone-replacement material.

Is device is preferably in the form of a syringe. As such, the surface area of the clotting agent exposed to the bone-replacement material is directly dependant on the volume of bone-replacement material loaded into the syringe. This allows for greater control of the amount of blood clotting agent to which the bone-replacement material is exposed.

The device of the present invention may further comprise a heating means associated with the chamber of the device. This can be used to heat the bone-replacement material up to physiological temperature; at the same time, the rate of blood clotting is increased. It is also possible to heat the bone-replacement material to a temperature greater than physiological temperature to promote the clotting of the blood and then to cool it either before or while delivering the bone-replacement material from the chamber.

In a fourth aspect, the present invention provides a method for producing a bone-replacement material, the method comprising:
(i) providing a solid material comprising calcium phosphate;
(ii) adding a liquid comprising blood and/or a processed blood product to the solid material to produce a solid/liquid mixture;
(iii) placing the solid/liquid mixture in the chamber of a device as herein described in relation to the third aspect of the present invention so as to contact the blood-clotting agent pre-loaded in the chamber and/or pre-coated on an interior surface thereof;
(iv) allowing the blood in the solid/liquid mixture to clot to produce a bone-replacement material; and
(v) removing the bone-replacement material from the device.

As is apparent from the above discussion, the possible ways described previously that the device of the present invention can be used are equally applicable to this method (and vice versa).

In the method of the present invention, the blood may be allowed to clot so that the bone-replacement material exhibits gel-like rheological behavior at physiological temperature.

EXAMPLES 10 cm$^3$ of 2 to 5 mm Actifuse® granules and a clotting agent were mixed in a sample tube with 10 cm$^3$ of fresh ovine blood drawn from the jugular vein. The tube was then agitated gently to mix the constituents and then set aside to clot. The clotting time was measured as the time taken for the blood to stop flowing around and through the granules. The clotting agents used and the results from each clotting agent are shown in Table 1. The wt % of the clotting agent is given as a weight percentage of the combined weight of the Actifuse® granules and the clotting agent.

| Example | Clotting agent | Wt % clotting agent | Clotting time (mins) |
|---|---|---|---|
| 1 | None | N/A | >20 |
| 2 | Calcium Chloride | 39.39% | 8 |
| 3 | Calcium Chloride | 19.06% | 4:20 |
| 4 | Calcium Chloride | 5.68% | 1 |
| 5 | Powdered Zeolite | 39.45% | 2:13 |
| 6 | Powdered Zeolite | 20.28% | 2:05 |
| 7 | Powdered Zeolite | 4.90% | 1:34 |

The invention claimed is:

1. A bone graft material for mixing with a blood product to produce a bone-replacement material, the bone graft material comprising granules of synthetic bone material, at least some of which have a solid coating comprising a blood-clotting agent, wherein:
the mass of blood-clotting agent in the bone graft material is 2% or more of the combined mass of the blood-clotting agent and the synthetic bone material;
the mass of the synthetic bone material in the bone graft material is 90% or more of the combined mass of the blood-clotting agent and the synthetic bone material; and
the blood clotting agent is either zeolite or zeolite and calcium chloride,
wherein the solid coating covers 50% or more of the outer surface of the synthetic bone material.

2. A bone graft material according to claim 1, wherein the mass of blood-clotting agent in the bone graft material is 5% or more of the combined mass of the blood-clotting agent and the synthetic bone material.

3. A bone graft material according to claim 1, wherein the bone graft material is for mixing with whole blood.

4. A bone graft material according to claim 1, wherein the synthetic bone material comprises calcium phosphate.

5. A method of forming a bone-replacement material, the method comprising mixing: (a) whole blood; and (b) the bone graft material of claim 1.

6. The method according to claim 5, wherein the synthetic bone material comprises calcium phosphate.

7. The method according to claim 5, wherein the bone graft material is a solid material.

8. The method according to claim 5, wherein the bone graft material comprises granules of synthetic bone material, at least some of which have a solid coating comprising the blood-clotting agent.

9. The method according to claim 5, wherein 1 part by weight of the bone graft material is added to 0.1 to 10 parts by volume of blood.

10. A device for delivering bone-replacement material to an area to be treated, the device comprising:
(i) a chamber for containing the bone-replacement material of claim 1, wherein the chamber is pre-loaded and/or pre-coated on an interior surface thereof with the blood-clotting agent;
(ii) means for introducing the bone-replacement material into the chamber to contact the blood-clotting agent; and
(iii) means for delivering the bone-substitute material from the chamber to the area to be treated.

11. The device according to claim 10, wherein the device is a syringe.

12. The device according to claim 10, wherein the chamber is further pre-loaded and/or pre-coated on an interior surface thereof with a dehydration agent.

13. The device according to claim 10, wherein the device further comprises heating means for heating the contents of the chamber.

14. A method for producing the bone-replacement material of claim 1, the method comprising: (i) providing a solid material comprising calcium phosphate; (ii) adding a liquid comprising blood and/or a processed blood product to the solid material to produce a solid/liquid mixture; (iii) placing the solid/liquid mixture in the chamber of a device as defined in claim 10 so as to contact the blood-clotting agent pre-loaded in the chamber and/or pre-coated on an interior surface thereof; (iv) allowing the blood in the solid/liquid mixture to clot to produce a bone-replacement material; and (v) removing the bone-replacement material from the device.

15. The method according to claim 14, wherein the solid in step (i) further comprises a dehydration agent.

16. A bone replacement material formed by the method of claim 5.

17. A bone graft material according to claim 4, wherein the synthetic bone material comprises hydroxyapatite.

18. A bone graft material according to claim 1, wherein the blood clotting agent is zeolite.

19. A bone graft material according to claim 1, wherein the blood clotting agent is zeolite and calcium chloride.

* * * * *